(12) United States Patent
Persson et al.

(10) Patent No.: US 6,640,150 B1
(45) Date of Patent: Oct. 28, 2003

(54) METHOD FOR PRODUCING A DENTAL FIRST ATTACHMENT PART FOR AN IMPLANT OR A SECOND ATTACHMENT PART, AND A HOLDER FOR A MODEL OF THE FIRST ATTACHMENT PART

(75) Inventors: Magnus Persson, Vänerborg (SE); Rickard Holmersson, Göteborg (SE)

(73) Assignee: Nobel Biocare AB, Göteborg (SE)

( * ) Notice: Subject to any disclaimer, the term of this patent is extended or adjusted under 35 U.S.C. 154(b) by 0 days.

(21) Appl. No.: 09/674,647

(22) PCT Filed: Apr. 27, 1999

(86) PCT No.: PCT/SE99/00680

§ 371 (c)(1),
(2), (4) Date: Nov. 2, 2000

(87) PCT Pub. No.: WO99/62422

PCT Pub. Date: Dec. 9, 1999

(30) Foreign Application Priority Data

May 29, 1998 (SE) .............................. 9801933

(51) Int. Cl.[7] .............................................. G06F 19/00
(52) U.S. Cl. ................................... 700/118; 433/213
(58) Field of Search .................. 700/117–119; 433/215, 433/213, 223, 214

(56) References Cited

U.S. PATENT DOCUMENTS

| | | | |
|---|---|---|---|
| 5,452,219 A | * 9/1995 | Dehoff et al. ............... | 700/163 |
| 5,587,912 A | 12/1996 | Andersson et al. ........... | 700/98 |
| 5,607,305 A | 3/1997 | Andersson et al. .......... | 433/223 |
| 5,733,126 A | 3/1998 | Andersson et al. .......... | 433/223 |
| 5,880,962 A | 3/1999 | Andersson et al. ........... | 700/98 |
| 5,938,446 A | * 8/1999 | Andersson et al. .......... | 433/223 |
| 5,993,214 A | * 11/1999 | Persson ...................... | 433/223 |
| 6,126,445 A | * 10/2000 | Willoughby ................. | 433/223 |
| 6,152,731 A | * 11/2000 | Jordan et al. ................. | 433/69 |
| 6,283,753 B1 | * 9/2001 | Willoughby ................. | 433/172 |
| 6,322,359 B1 | * 11/2001 | Jordan et al. ................. | 433/73 |
| 6,424,877 B1 | * 7/2002 | Kondo et al. ............... | 700/117 |

* cited by examiner

Primary Examiner—Albert W. Paladini
Assistant Examiner—Zoila Cabrera
(74) Attorney, Agent, or Firm—Swidler Berlin Shereff Friedman, LLP

(57) ABSTRACT

An attachment part for an implant or second attachment part can be produced at a production station. The external shape of the attachment part is scanned at a scanning station at which a wax model is used. The scanned information is digitized and transmitted to the production station. An insert which has the surface configuration of the implant or of the second attachment part is selected from among a number of units having different possible surface configurations. The unit is applied in or on a holder which is centered on a turntable. The holder is provided with or operates with or operates with orientation information for the holder relative to the table. The model which is designed as a wax model is applied on the holder over the unit. The turntable is rotated and the external shape of the wax model is scanned. A blank with a pre-produced surface configuration which corresponds to the said selected surface configuration is machined in the machining equipment with the aid of the digitized information and the said rotation information.

20 Claims, 3 Drawing Sheets

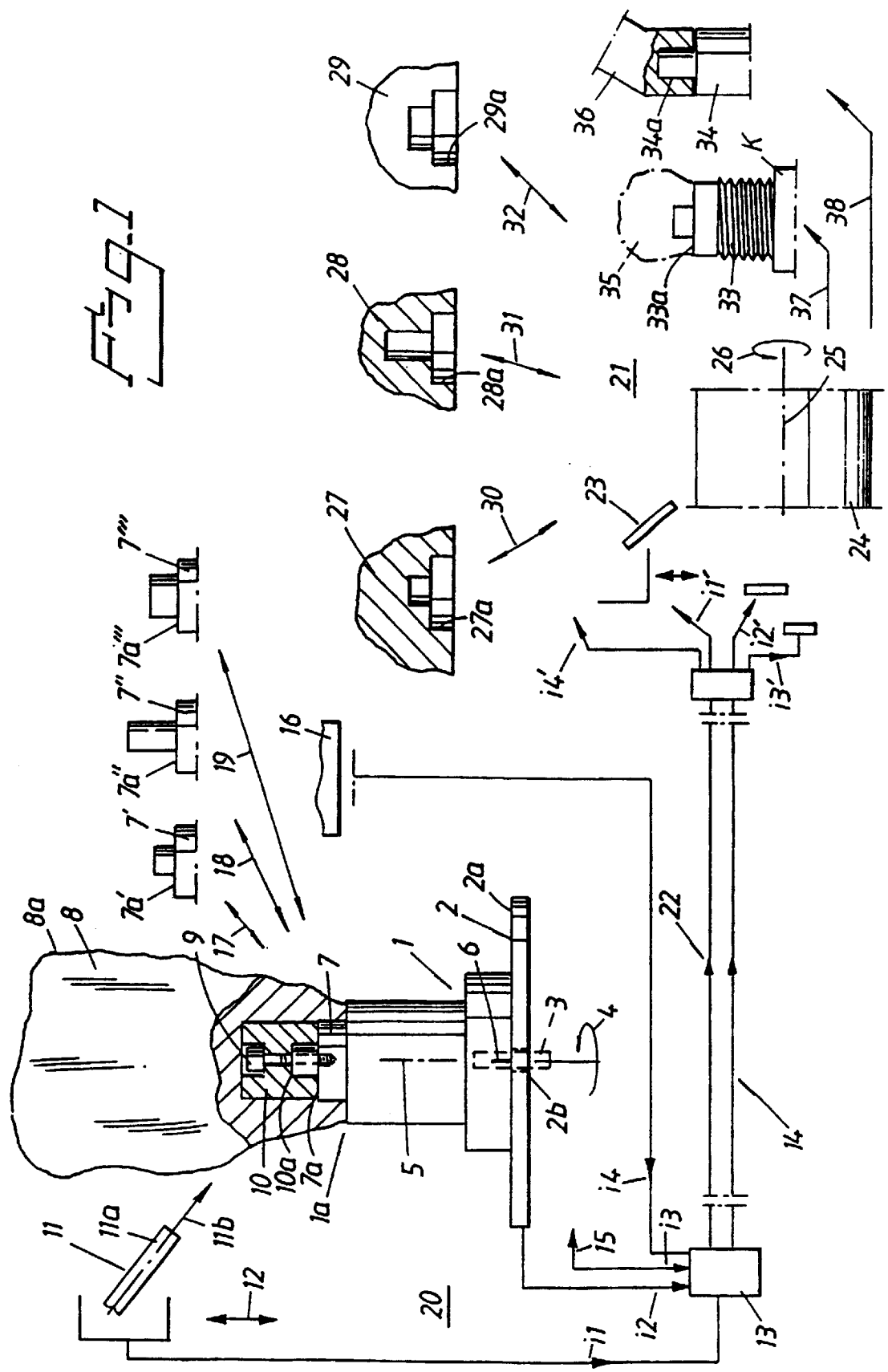

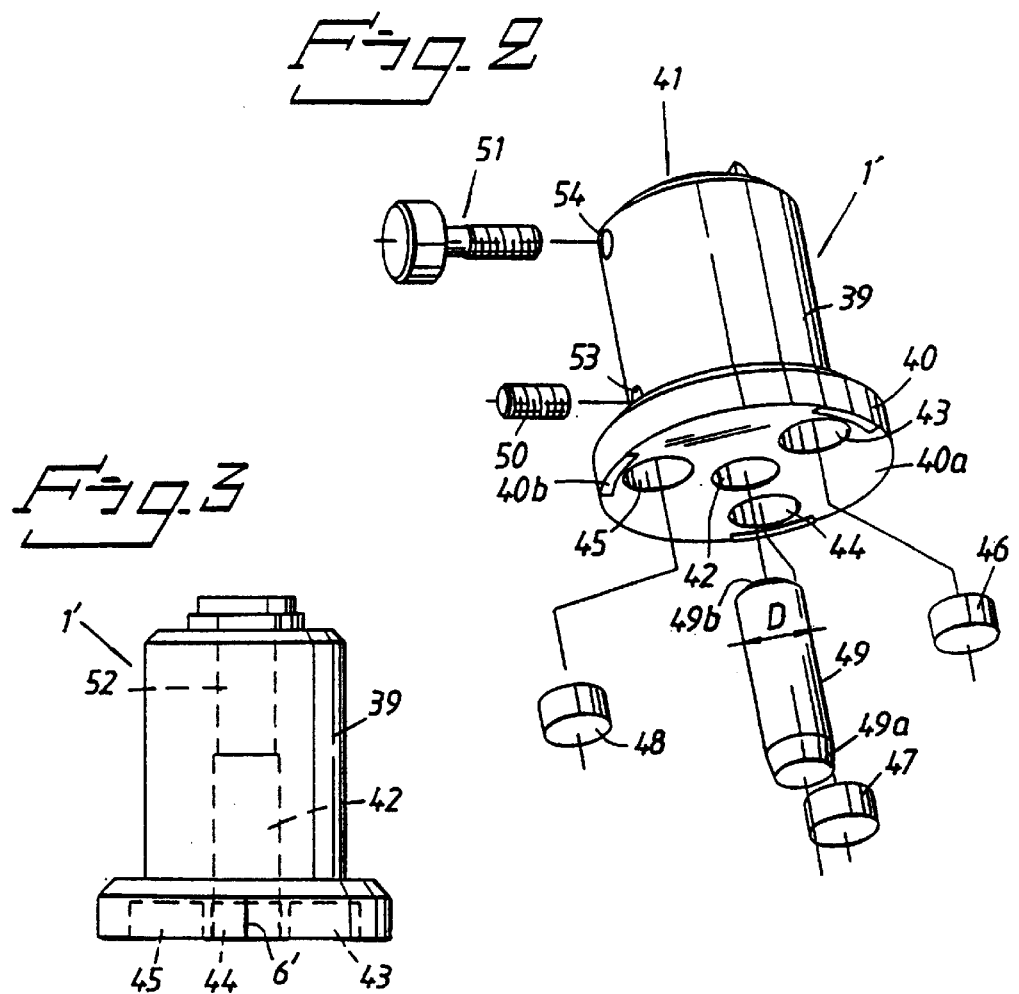
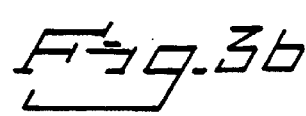
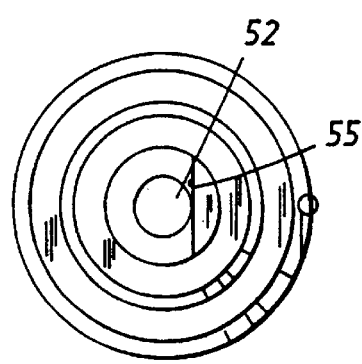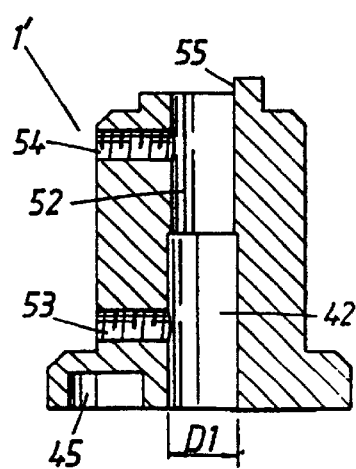

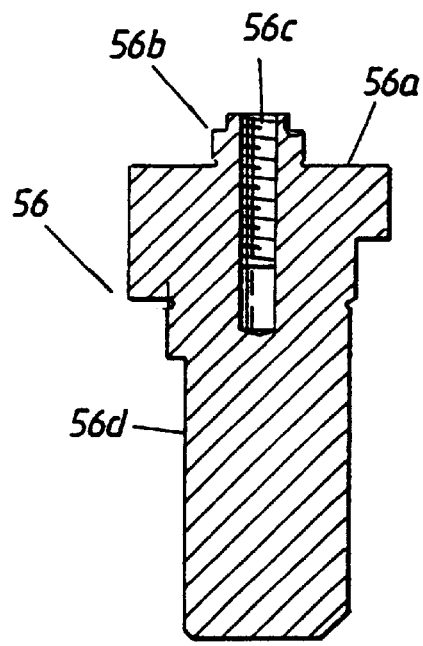
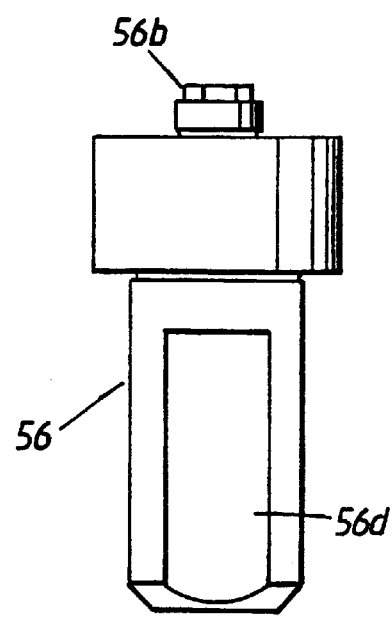
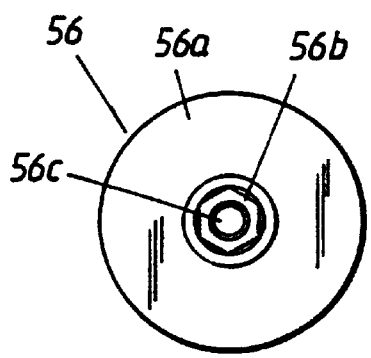
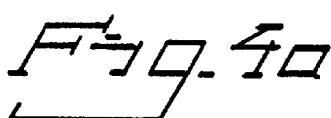
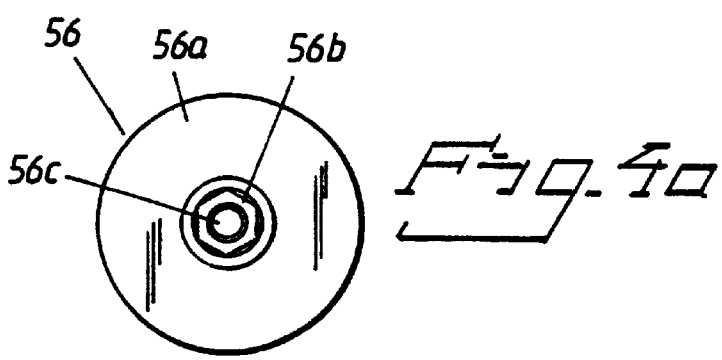
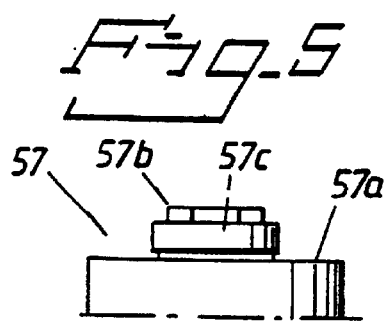
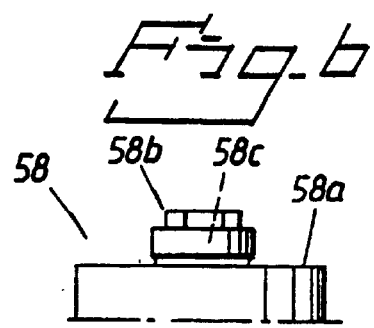

METHOD FOR PRODUCING A DENTAL FIRST ATTACHMENT PART FOR AN IMPLANT OR A SECOND ATTACHMENT PART, AND A HOLDER FOR A MODEL OF THE FIRST ATTACHMENT PART

TECHNICAL FIELD

The present invention relates to a method for producing a dental first attachment part for an implant in a jaw bone or for a second attachment part. Examples of a first attachment part which may be mentioned are a spacer, including individual spacers and temporary spacers, prosthetic constructions, tooth replacements in different forms, etc. According to the method, a model of the external shape of the first attachment part is scanned at a scanning station and the scanned information is digitized and transmitted in whole or in part on telecommunications and/or data link(s) to a production station. At the latter, a blank is machined in machining equipment so that the said external shape is applied to the blank. The invention also relates to a holder permitting application of a wax model of the external shape to a first attachment part, which can be of the said type. The first attachment part is connected or can be connected to an implant in the jaw bone or to a second attachment part. The holder also permits its application to a turntable so that the said external shape can be scanned by means of scanning equipment upon rotation of the table and holder.

PRIOR ART

It is already known to scan models of different types at scanning stations of dental technicians or dentists and to transmit a digitized version of the scan via a telecommunications and/or data link, for example the Internet, to a production station. It is also already known to apply the model to a holder which is rotated by means of a turntable during scanning. Reference may be made here to the PROCERA production system which is available on the market for products that are used in dentistry. In the said system, the blank is machined as a function of the digitized information received.

DESCRIPTION OF THE INVENTION
TECHNICAL PROBLEM

There is a need to be able to offer technically simple components allowing straightforward handling and manoeuvring in conjunction with the production of attachment parts of the type in question. The invention aims to solve this problem, among others.

There is a need to be able to offer a holder for different wax models which is easy and straightforward to use for the dental technician/dentist and with the aid of which the scanning function can be effected in a technically straightforward manner and so that it can be transmitted to a production station for production, from the blank, of a product having the external shape of the model. The invention solves this problem too.

In order to be able to transmit clear information with very great tolerance requirements in respect of the produced product (the attachment part), it is important, in the scanning principle which is based among other things on rotation of the scanned model, to be able to obtain an exact centring of the wax model and for the position of rotation or position of orientation of the model on the table to be coordinated or synchronizd with the position of rotation of the production unit for the rotatable blank which is to be milled. It should be noted here that accuracies of values around ²⁄₁₀₀mm must be possible. The invention aims to solve this problem too.

It must also be possible for the model being used to be held exactly in the holder, and in this connection use is made of the realization that employing a range of inserts (or corresponding units) greatly simplifies the production of the contact surfaces in question. The attachment or securing of the respective selected insert is thus of crucial importance. The invention also solves the problems in these respects.

It is also important to be able to arrange the exchangeable inserts or units with respect to rotation and vertical setting. The invention solves this problem too.

SOLUTION

The feature which can principally be regarded as characterizing a method according to the invention is that a unit which has the surface contact configuration of the implant or of the second attachment part, respectively, is selected from among a number of units with different surface contact configurations. The unit is applied in a holder which is centred on a turntable and is provided with or operates with angle-of-rotation information (information on the orientation of the holder on the table). A further feature is that the model is designed as a wax model which is applied on the holder over the unit with the selected surface contact configuration, after which the turntable is rotated and the external shape of the wax model is scanned. A further feature is that a blank with a pre-produced surface contact configuration which corresponds to the said selected surface contact configuration is machined in the machining equipment with the aid of the transmitted digitized information and the transmitted angle-of-rotation information (orientation information in the direction of rotation relative to the table).

In one embodiment, a blank is selected from among a number of blanks which have been pre-produced with different surface contact configurations, the said selected blank having a surface contact configuration which corresponds to the surface contact configuration of the unit in question.

A holder according to the invention can principally be regarded as being characterized in that it has bearing spaces for the unit or insert which can be selected from a number of units or inserts with different (possible) surface contact configurations for the implant or the abovementioned second attachment part. A further feature is that the wax model can be applied to the holder over the surface contact configuration on the selected unit or insert. For its centring and rotational orientation on the turntable, the holder is further provided with or cooperates with centring members or a function marking the angle of rotation.

In one embodiment, the holder has, on its underside, a recess for a centring pin incorporated in or forming the centring members which can be activated upon centring of the holder in the turntable. In a further embodiment, the holder is provided, on its underside, with one or more magnets for securing the holder to the turntable in a predetermined angle-of-rotation position which can be adjusted by means of one or more markings or indications arranged on the holder. The holder can be arranged in such a way that the respective unit or insert can be locked in a set selectable vertical position in association with the said bearing space. The wax model can be screwed to the unit by means of a screw which can be screwed in a thread in the unit or the insert. The said thread in this case corresponds with a thread arranged in the implant or in the second attachment part. The holder can also be arranged with a locking screw for the selected unit or insert. In addition, the centring pin can be adjustable, with respect to its position projecting from the holder, by means of a further locking screw. The angle of rotation of the respective unit or insert in the holder is preferably fixed in position in the holder.

ADVANTAGES

By means of what has been proposed above, a holder is provided on whose upper side different inserts or units can be applied. The inserts represent different surface contact configurations which are used in the system. The respective wax model can be applied on the holder, and its external shape can be transmitted to the production station which uses blanks with corresponding prepared surface contact configurations, one of which is selected in each case. Known scanning principles which give a small amount of scanned information despite high accuracy requirements in respect of the product can be used. The dental technician or equivalent obtains an easy-to-manage holder function for wax models which can be applied to different types of spacers, including individual spacers and temporary spacers, different prosthesis components and implant systems and parts thereof. It is possible to easily adjust the height of the respective insert or unit in the holder. The bearing pin arrangement which is used can be adapted to different types of turntables.

DESCRIPTION OF THE FIGURES

A presently proposed embodiment of a method and a holder according to the invention will be described below with reference to the attached drawings, in which:

FIG. 1 shows, in an explanatory sketch, a production system for second attachment parts according to the above, where holder, turntable, wax model, scanning equipment, selection function for different inserts for the holder, signal transmission and modem are arranged at a scanning station, digitized information can be transmitted on one or more links, and signal resolution equipment, machining equipment and different blanks are shown at a production station, and where products made at the production station have been transferred to the context in which they are used, FIG. 2 shows, in a perspective view, and seen at an angle from below, the structure of a holder with bearing pin for application to a support table, and with magnet arrangement for retaining the set angle-of-rotation position on the turntable, FIGS. 3–3b show the holder according to FIG. 2 in a side view, an end view and a vertical cross section, respectively, FIGS. 4–4b show, in a vertical cross section, an end view and a side view, respectively, a structural design of an insert which can be applied in the holder according to FIGS. 2–3b, FIG. 5 shows, in a side view, parts of an insert which differs from the insert according to FIGS. 4 4b, and FIG. 6 shows, in a side view, parts of a further structural design of an insert which differs from the inserts according to FIGS. 4–4b and 5.

DETAILED EMBODIMENT

In FIG. 1, a holder 1 according to the invention is arranged on a turntable 2. The turntable can be of a types known per se. The members effecting the rotation are not shown for reasons of clarity. The holder is centred on the table by centring member 3 (which is described in more detail below) and rotation 4 is effected about an axis of rotation 5 which coincides with the centre axis of the holder.

The holder has an indication or marking 6 by means of which the position of rotation or angle of rotation of the holder can be oriented on the supporting surface 2a of the rotation member 2.

The holder is arranged so as to receive or bear, on its upper part 1a, an insert 7 with a surface contact configuration 7a which is specific to the insert. Mounted on the holder, over the said insert, is a wax model 8 which has an external surface 8a. The model is screwed into the insert by means of a screw. The model is provided with a fastening member 10 which is fixed to the model and which has a contact surface 10a which corresponds with the surface 7a of the insert. The screw extends through a recess in the fastening member and its external thread cooperates in an internal thread in the insert 7.

The insert 7 is selected from among a number of different inserts, each one of which can be applied to the holder. A number of alternative inserts have been designated 7', 7", 7''' etc. The inserts differ from one another in their different surface contact configurations 7a, 7a', 7a", 7a''', etc. The securing part on the inserts is essentially identical and is described below.

The external surface 8a of the wax model is scanned by scanning equipment which has been symbolized by 11. The equipment can comprise a scanning needle 11a cooperating with the external surface, a scanning function with optical beam 11b, etc. In the present case, scanning takes place in the polar coordinates system. The equipment 11 is moved in the vertical direction at the same time as the model is rotated with the table 2 and the holder 1. This scanning principle is well known from the PROCERA system. Other types of scanning systems can also be used in the present case. The result of the scanning consists of digitized information i1 which is fed to adapter equipment 13 which can be of a type known per se and include a modem for connection to telecommunications and/or data links which are symbolized by 14. The connection can in this case be made via the public telecommunications and data link networks (e.g. the Internet).

The information transmitted via the link 14 can also include information i2 on speed of rotation, information i3 on position of rotation of the holder relative to the turntable and/or information i4 on the selected insert 7, 7', 7", 7'''. The rotation information can be obtained by means of rotation-sensing members (not shown) which can be of a type known per se, the orientation position can be obtained by contact and/or detection members 15, and the type of insert 7, 7', 7", 7''' can be indicated, for example, via manual actuation member 16. The selection possibilities for the inserts or units are symbolized by arrows 17, 18 and 19.

A scanning station, for example at the workplace of a dental technician or dentist, is shown by 20, and a production station which serves a number of dental technicians or dentists is shown by 21. At the production station, the information items transmitted digitally on the link 14 are separated out. A first information item i1' can be allocated to the scanning information i1 and controls the machining equipment 23. Scanning angles on the scanning equipment and machining angles in the machining equipment can in this case be selected to be essentially the same, for example 45°. The machining at the production station 21 can, however, be done in other coordinates systems without deviating from the concept of the invention. The information item i2' separated out at the receiving station receives the rotation information i2 from the scanning station. The blank 24 can thus be rotated at a speed which is related to the speed of the turntable. The blank 24 is rotated about its centre axis 25 in a direction of rotation. The information item i3' separated out at the receiving station corresponds to the orientation function for the holder relative to the turntable. The information item i3' can coordinate the scanning and machining functions so that the external shape 8a can be followed and produced. The information item i4' corresponds to the information i4 from the scanning station and can be applied for selecting the blank which is related to the insert or unit arranged in the holder 1 in the particular case. At the machining station, the blanks 27, 28, 29 are machined in advance with surface contact configurations 27a, 28a and 29a which correspond to the surface contact configurations 7a', 7a" and 7a''', respectively, etc. Thus, depending on the information received, blank 27, 28 or 29 having the surface contact configuration corresponding to the scanned information is selected. The selection function is indicated by 30, 31 and 32.

The finished product, for example in the form of a spacer (various types thereof), ceramic product, etc., can thereafter be arranged on the dental unit in question, for example an implant 33, spacer 34, etc. According to the figure, the finished product can consist of a prosthesis structure 35 on the implant 33 or of a second attachment part 36 which can be connected to the first attachment part 34, etc. The transfer from production to the dental element in question 33, 34, etc., is symbolized by arrows 37 and 38 and can be done by conventional means, for example the postal service, i.e. the finished product is returned to the scanning station by some or other means.

In FIG. 2, the holder is indicated by 1'. The holder comprises an essentially cylindrical upper part 39 and base part 40. Each of the said spacers can be placed on the upper surface 41, in a recess. The holder has a central recess 42 which opens out on the underside 40a of the base part. Also arranged on the underside are recesses 43, 44 and 45 for magnets 46, 47 and 48, respectively. The magnets are secured in the recesses and are arranged to retain the holder in the applied angle-of-rotation position on the turntable, which is made of metal or comprises a metal plate on which the holder can be mounted. The base plate 40a of the holder is provided with parts 40b alongside the recesses 43, 44, 45, and the arrangement is such that closed magnetic circuits are established in the holder and the turntable. The closed magnetic circuits seek to retain the holder in the mounted angle-of-rotation position. The arrangement is also such that the holder can be turned manually counter to the action of the magnetic forces until the desired orientation position relative to the turntable has been reached. A bearing or centring pin 49 which can be arranged in the recess 42 is designed with a diameter D which, with great precision, for example precision of 0.1 mm, can be fitted in the recess 42. The pin also fits in a bearing recess 2b (see FIG. 1) in the turntable and, when the holder is mounted on the table, the pin extends partially out of the recess 42 and down into the said recess 2b. The pin fits in the table recess with great precision, for example precision of 0.1 mm. The position of insertion of the pin 49 in the recess 42 can be determined by a locking screw 50. The pin is provided with guiding bevels 49a, 49b. At its upper part, the holder is also provided with a further locking screw 51, by means of which the respective insert or unit can be vertically adjusted, as is explained below.

According to FIGS. 3, 3a and 3b, the holder comprises a recess 52 which adjoins the recess 42 and is intended for the said inserts, as is explained below. On the base part, the holder is provided with a marking or indication, which here has the reference 6'. The holder is provided with a first threaded hole 53 for the locking screw 50 and with a second threaded hole 54 for the locking screw 51. In addition, there is a surface 52 which fixes the angle of rotation and by means of which the respective insert or unit is held, as is explained below, in a defined angle-of-rotation position in the holder. The diameter D1 of the recess 42 is shown in FIG. 3b.

FIGS. 4, 4a and 4b show an example of a first insert or unit 56 (cf. insert 7, 7', 7", 7''' above). The insert 56 has a surface contact configuration 56a and an upwardly projecting anchoring part 56b which is provided with a central threaded recess 56c extending partially down in the insert or the unit. The anchoring part forms part of the surface contact configuration. The insert has a bevelled surface 56d which cooperates with the surface 55 of the holder (see FIGS. 3a and 3b). The lower parts of the insert according to FIGS. 4 and 4b can be pushed down into the recess 52 in the holder 1' (see FIGS. 3 and 3b).

FIGS. 5 and 6 show the designs of two further inserts 57 and 58 which can be applied in the holder and which are provided with varying surface contact configurations 57a, 58a and 57b, 58b respectively. The threaded hole 57c can also differ in size (diameter). The lower parts of the inserts are identical and can be inserted in the recess 52.

By means of this arrangement, the holder is centred on the turntable with the pin 49, which in turn is centred in the holder. The holder is in this way held in its centred position on the table. According to the above, the angle of rotation of the holder has been oriented relative to the table or its upper surface with the aid of the marking 6', and the information on the set position of rotation at the scanning station can be transmitted to the production station or is predetermined. The information on the position of rotation is set in relation to the starting position in the machining function at the production station. The height of the respective insert can be adjusted with the screw 51. The bearing pin 49 is in principle exchangeable in order to be able to be adapted to different types of turntable. A jaw bone is symbolized by K in FIG. 1, where the implant 33 has been partially screwed down into the jaw bone in question. The surface contact configuration of the implant is indicated by 33a and the surface contact configuration of the second attachment part is indicated by 34a. In one embodiment, the bearing recess 42 is designed with a greater diameter than the bearing recess 52.

The invention is not limited to the embodiment which has been described above by way of example, and instead it can be modified within the scope of the attached patent claims and the inventive concept.

What is claimed is:

1. A method for producing a first dental attachment part operative to engage an implant in a jaw bone or a second dental attachment part, the method comprising:
   arranging a holder on a turntable;
   selecting an insert member having a surface contact configuration of the implant or second dental attachment part, wherein the insert member is selected from a plurality of inserts having different surface contact configurations;
   arranging an insert member in or on the holder;
   arranging a model of an external shape of the first dental attachment part on the insert;
   determining orientation information of the model with respect to a scanner;
   rotating the turntable and simultaneously scanning the model of the external shape of the first dental attachment part at a scanning station;

digitizing the scanned information;
transmitting at least a portion of the digitized information and orientation information to a production station; and
machining at the production station a blank having a contact configuration similar to the insert to reproduce the external shape utilizing the orientation information.

2. The method according to claim 1, wherein the orientation information comprises an angle formed by a longitudinal axis of the first dental attachment part and a longitudinal axis of a probe of the scanning station.

3. The method according to claim 1, wherein the holder is centered on the turntable.

4. The method according to claim 1, wherein the first dental attachment part comprises a spacer, a prosthetic construction, or a tooth replacement.

5. The method according to claim 1, wherein the digitized information is transmitted over at least one of a telecommunications and a data link.

6. The method according to claim 1, wherein the model is a wax model.

7. The method according to claim 1, wherein the blank is selected from a plurality of inserts having different surface contact configurations corresponding to the surface contact configuration of the insert.

8. The method according to claim 1, wherein the orientation information comprises angle-of-rotation information or the orientation information is transmitted from the scanning station to the production station, and wherein the orientation information of the scanning function and of the production function are coordinated/synchronized.

9. A holder, comprising:
a first engaging surface operative to engage a wax model of an external shape of a first dental attachment part, wherein the first dental attachment part is operative to be connected to an implant in a jaw or to a second dental attachment part;
a second engaging surface operative to engage a turntable so that the external shape can be scanned by scanning equipment during rotation of the turntable;
a first bearing recess operative to receive an insert having a surface contact configuration of the implant or second dental attachment part, wherein the insert is selected from a plurality of inserts having different surface contact configurations for the implant or the second attachment part, and wherein the insert is operative to engage the wax model; and
at least one centering and orienting element operative to center and rotationally orient the holder relative to the turntable.

10. The holder according to claim 9, wherein the first dental attachment part comprises a spacer, an individual spacer, a temporary spacer, a prosthetic construction, or a tooth replacement.

11. The holder according to claim 9, wherein the centering and orienting element receives a centering member centered on the turntable.

12. The holder according to claim 9, wherein the centering and orienting element comprises a marking operative to facilitate aligning the holder with the turntable.

13. The holder according to claim 9, wherein the centering and orienting element comprises a centering member extending from the holder and the turntable.

14. The holder according to claim 9, wherein the insert can be locked in the set vertical position in association with the bearing space.

15. The holder according to claim 9, further comprising:
a second bearing recess in an underside of the holder, wherein the centering and orienting element comprises a centering pin received by the second bearing recess.

16. The holder according to claim 15, further comprising:
locking screws for the insert or the centering pin.

17. The holder according to claim 15, wherein the second bearing recess has a diameter greater than the first bearing recess.

18. The holder according to claim 9, further comprising:
at least one magnet operative to secure the holder to the turntable in a predetermined angle of rotation; and
a marking on a lower part of the holder operative to permit the angle of rotation to be adjusted.

19. The holder according to claim 9, wherein the wax model can be screwed to the insert with a screw that can be screwed in a thread in the insert, the thread corresponding to a thread arranged in the implant or in the second attachment part.

20. The holder according to claim 9, wherein the first bearing recess is operative to cooperate with a bevel on the insert in order to fix an angle of rotation of the insert relative to the holder.

* * * * *